United States Patent [19]

Berkovits et al.

[11] Patent Number: 4,577,633
[45] Date of Patent: Mar. 25, 1986

[54] RATE SCANNING DEMAND PACEMAKER AND METHOD FOR TREATMENT OF TACHYCARDIA

[75] Inventors: Barouh V. Berkovits, Newton Highlands, Mass.; Menashe B. Waxman, Toronto, Canada; William J. Combs, Shoreview, Minn.

[73] Assignee: Medtronic, Inc., Minneapolis, Minn.

[21] Appl. No.: 594,606

[22] Filed: Mar. 28, 1984

[51] Int. Cl.⁴ .............................................. A61N 1/36
[52] U.S. Cl. .............................................. 128/419 PG
[58] Field of Search ................ 128/419 PG, 702–706, 128/708

[56] References Cited

U.S. PATENT DOCUMENTS

| | | | |
|---|---|---|---|
| 3,698,398 | 10/1972 | Berkovits | 128/422 |
| 3,857,399 | 12/1974 | Zacouto | 128/419 |
| 3,939,844 | 2/1976 | Pequignot | 128/419 |
| 3,942,534 | 3/1976 | Allen et al. | 128/419 |
| 4,022,192 | 5/1977 | Laukien | 128/706 |
| 4,181,133 | 1/1980 | Kolenik et al. | 128/419 |
| 4,280,502 | 7/1981 | Baker et al. | 128/419 |
| 4,307,725 | 12/1981 | Sowton et al. | 128/419 |
| 4,312,356 | 1/1982 | Sowton et al. | 128/419 |
| 4,398,536 | 8/1983 | Nappholz et al. | 128/419 |
| 4,407,289 | 10/1983 | Nappholz et al. | 128/419 |
| 4,408,606 | 10/1983 | Spurrell et al. | 128/419 PG |

OTHER PUBLICATIONS

Camm, J. et al., "A Microcomputer-Based-Tachycardia Termination System—A Preliminary Report" J.M.E. & T., 4(2): 80–82, (1980).
Haffajee, C., "Self-Adapting Overdrive Demand Pacing as a Method for Terminating Ventricular Tachycardia" JACC 3(2): 555, (Feb. 1984).
Guize, L. et al., "Un Nouveau Stimulateur du Coeur: Le Pacemaker Orthorythmique", La Presse Medicale 79 (46): 2071–2072, (translation attached), (Oct. 1971).
Perticone, F. et al., "Standby Automatic Antiarrhythmic Device for Cardiologic Departments, PACE 4(3): A-65 (May–Jun. 1981).
Zacouto, F. et al., "Orthorhythmic Pacing in Arrhythmias", Am. J. Cardiol., 31, 165 (1973).
Zacouto, F. I. et al., "Improved Control of Recurrent Tachycardias by Automatic Orthorhythmic Pacing", Circulation (Oct. 1974).
Orthorhythmic Pacemaker C.S.O., Savita Laboratory (literature) Oct. 1974.
Luderitz, B. et al., "The Use of Programmed Rate-Related Premature Stimulation in Managing Tachyarrhythmias", Cardiac Pacing Diagnostic and Therapeutic Tools, 538(455): 227–234 (1976).
Mandel, W. J., et al., "Recurrent Reciprocating Tachycardias in the Wolff-Parkinson-White Syndrome, Control by the Use of a Scanning Pacemaker", CHEST 69(6): 769–774, (Jun. 1976).

*Primary Examiner*—William E. Kamm
*Attorney, Agent, or Firm*—Joseph F. Breimayer; John L. Rooney; Robert C. Beck

[57] ABSTRACT

A self-adapting demand pacemaker that recognizes the tachycardia from the intrinsic signals and initiates treatment in the following manner: First, the escape interval of the demand pacemaker is shortened to be identical to the cycle length of the tachycardia, then to overdrive the tachycardia the pacemaker escape interval is continuously shortened with each subsequent beat, for a predetermined number of beats, by a small programmable decrement. Thereafter, the escape interval is restored to its original value and protects against a potential bradycardia. It has to be emphasized that the pacemaker remains in demand mode all of the time; thus stimulation in a vulnerable zone is prevented and some of the hazards that accompany overdrive pacing are reduced. An additional advantage of this treatment is that since each stimulus is delivered only a few milliseconds before the next intrinsic depolarization is expected to arrive at the site of the electrode, it facilitates capture even when the excitable interval is extremely short.

29 Claims, 3 Drawing Figures

RATE SCANNING DEMAND PACEMAKER AND METHOD FOR TREATMENT OF TACHYCARDIA

BACKGROUND OF THE INVENTION

1. Field of the Invention

This invention relates to a method and apparatus for control of tachycardia, particularly ventricular tachycardias.

2. Description of the Prior Art

Tachycardia is a condition in which the atria, ventricles or both chambers of the heart beats very rapidly, and not within the normal physiological range, typically exceeding 160 occurrences per minutes. Atrial tachycardia is the medical term assigned to the condition in which rapid and regular succession of P waves of the PQRST waveform complex occur. The rate of occurrence is in excess of the physiological range normally encountered in the particular patient.

Paroxysmal supra-ventricular tachycardia is the medical term assigned to the condition in which there is a sudden attack of rapid heart action in the atria or in the atrial-ventricular node. The main characteristics are the same as those in atrial tachycardia.

Normally atrial tachycardia and paroxysmal supra-ventricular tachycardia is not a life threatening condition, unless it progresses into ventricular tachycardia or fibrillation. Ventricular tachycardia is the medical term assigned to the condition in which rapid and regular succession of R waves of the PQRST waveform complex occur. Again, the rate of occurrence is in excess of the physiological range of the particular patient and can, if left untreated, progress into ventricular fibrillation. In ventricular fibrillation, the ventricles are unable to pump blood in a coordinated fashion and heart output drops to a level dangerous to the patient.

Typically, these life-threatening conditions of ventricular tachycardia or ventricular fibrillation must be treated by drug therapy or by electrical stimulation, such as cardioversion or defibrillation, and the patient is confined for some time in the hospital.

In the past 15 years, attention has been paid to the use of lower energy stimulation to treat each of the above mentioned tachycardia conditions. Initially, investigators employed asynchronous pacemakers which were triggered typically by the patient into asynchronous pacing at a low rate, for underdrive pacing, or at a high rate, for overdrive pacing. Such pacing was accomplished in the hospital setting by a temporary pacemaker and catheter operated by the physician or permanent pacemakers and leads were implanted in the patient which could be activated by a magnet applied over the pacemaker by the patient when the patient felt a tachycardia condition. In addition, certain pacemakers were devised to detect a tachycardia condition and deliver a stimulus to either cardiovert, underdrive or overdrive the heart (see for example Gemmer, U.S. Pat. No. 3,460,542 and Zacouto U.S. Pat. No. 3,857,399).

In the Berkovits U.S. Pat. No. 3,698,398, one of the co-inventors of this invention proposed that atrial tachycardia and paroxysmal supra-ventricular tachycardias be treated by a pacemaker, either implantable or external, which when actuated by a sensed tachycardia condition, would deliver a burst of stimuli to the atria. That invention further contemplated that the interval between successive stimuli would either be increased or decreased in a progressive manner so that one of the intervals in the succession of intervals would be the critical interval that it would allow interruption of the tachycardia mechanism. That modality has been called rate scanning or entrainment of the tachycardia interval.

More recently, rate scanning has been implemented in microcomputer based tachyarrhythmia termination systems, such as the Medtronic Model SPO 500 antitachyarrhythmia system. Another system which has been recorded in the article entitled, "A Microcomputer-Based Tachycardia Termination System—A Preliminary Report", by J. Camm et al in the *Journal of Medical Engineering and Technology*, Vol. 4, No. 2, March 1980, the authors' report on their experience with a rate scanning regimen which was programmed through a microcomputer system. Very generally, the authors define their system as auto-decremental pacing which involves:

1. Sensing and recognition of tachycardia, defined for this specific purpose as four consecutive P-P intervals between 218 and 375 ms.
2. Pacing on an initial discharge interval equal to the P-P interval-tachycardia cycle length (TCL) minus a decrement value (D). The discharge interval of the pacemaker pace and cycle length (PCL) progressively shortens as with each subsequent beat an additional decrement is subtracted. The minimum PCL of the pacemaker is 280 ms.
3. The pacing sequence continues until the next discharge interval would prolong the total duration of pacing beyond a preset period (P). P and D are operator controlled variables.

The pacemaker hardware employed by the authors consisted of a microcomputer unit based on a Signetics 2650 eight bit microprocessor which controls an isolated stimulation module. The input to the microcomputer was derived from the threshold detector output of an isolation amplifier. Both the stimulator and receiver module were part of a device Neurolog 4279 arrhythmia investigation system. A Hewlett-Packard 9830 desktop calculator was programmed to simulate the performance of the auto decremental pacing system. The autodecremental modality for tachycardia termination was assessed and selected patients with paroxysmal supra-ventricular tachycardia. Two bipolar electrocatheters were introduced percutaneously for sensing and pacing purposes. Autodecremental atrial pacing with P values between 2 and 5 seconds and D values between 3 and 20 ms terminated all tachycardias without initiating other atrial tachyarrhythmias.

The authors of this article go on to state that this system had proved successful in the conversion to sinus rhythm of a variety of supra-ventricular tachycardias.

The literature generally suggests that overdrive burst stimulation or rate scanning stimulation may he used for either atrial or ventricular tachyarrhythmia conditions. However, actual reported experience of use of rate scanning or burst overdrive stimulation to treat ventricular tachycardia successfully is scant indeed. Most investigators have confined their efforts to the treatment of atrial or supra-ventricular tachycardias due to the danger involved in stimulating into the vulnerable zone of the ventricular tachycardia cycle and initiating fibrillation. The present invention overcomes that danger through the relatively straightforward technique of sensing natural depolarizations of the ventricle during the rate scanning interval and resetting the rate scanning time interval in response thereto to thereby avoid competitive pacing.

SUMMARY OF THE INVENTION

In accordance with the present invention, a method and apparatus for the control of a ventricular tachycardia is disclosed which comprises means or steps for: sensing natural heart depolarizations and providing a sense signal in response thereto; confirming a tachycardia condition; generating a burst of a plurality of spaced heart stimulating pulses which potentially allow tachycardia to be terminated; establishing the escape intervals between the plurality of spaced heart stimulating pulses; and restarting the escape interval in the event that a natural heartbeat is sensed during the provision of said burst of heart stimulating pulses, whereby the provision of a stimulating pulse into a vulnerable phase of the heart cycle is avoided. The device or method contemplates programmable control means for controlling the operating parameters of sensing means, confirming means, pulse generating means, timing means and other characteristics of the operation of the device. The device or method further incorporates a bradycardia pacing system including a bradycardia escape interval timer and means for programming the bradycardia escape interval. In addition, the method and apparatus contemplates the provision of a rate scanning burst of stimulus wherein the intervals between successive sense signals are measured and tachycardia is confirmed as a function of the measured intervals. Once the tachycardia is confirmed, the method and apparatus contemplates generating a stimulating pulse at the end of a first interval measured from the last sensed sense signal and applying the pulse to the heart, and generating the further stimulating pulses in the series of pulses constituting the burst at the end of further intervals measured from the generation of the preceding stimulating pulse or the last sensed signal, whichever occurs later, and wherein the further time intervals are decreased by a decrementing factor to effect a rate scanning technique. In accordance with the invention, the decrement factor and the number of impulses in a burst may also be programmed.

In accordance with the invention, tachycardia is confirmed by measuring the beat-to-beat intervals and/or the rate of change of the beat-to-beat intervals, comparing the measured values against a programmed threshold value in a memory register and counting those intervals or rate of changes that exceed the thresholds. When the count reaches a further value equal to a programmed count stored in a register, then tachycardia is confirmed.

These and other features and advantages of the present invention will be apparent from the following drawings and description.

DESCRIPTION OF THE PREFERRED EMBODIMENT

The method of the present invention is practiced with apparatus which is currently available from Medtronic, Inc. and Hewlett-Packard Corporation and with the use of the computer program appended to this application. In reference to FIG. 1, the system comprises the Hewlett-Packard HP85 minicomputer 10 the patient interface module 30 and the stimulation protocol executor or controller 50. The patient interface module 30 is otherwise known as the Medtronic ® Model 2319A which is used in conjunction with the stimulation protocol executor 50 which are collectively referred to as the Medtronic Model 2319 Custom Programmable Stimulator. The following description of the system has been taken from the Medtronic ® Model 2319 Custom Programmable Stimulator Technical Manual, copyright February 1983.

Figure 1:
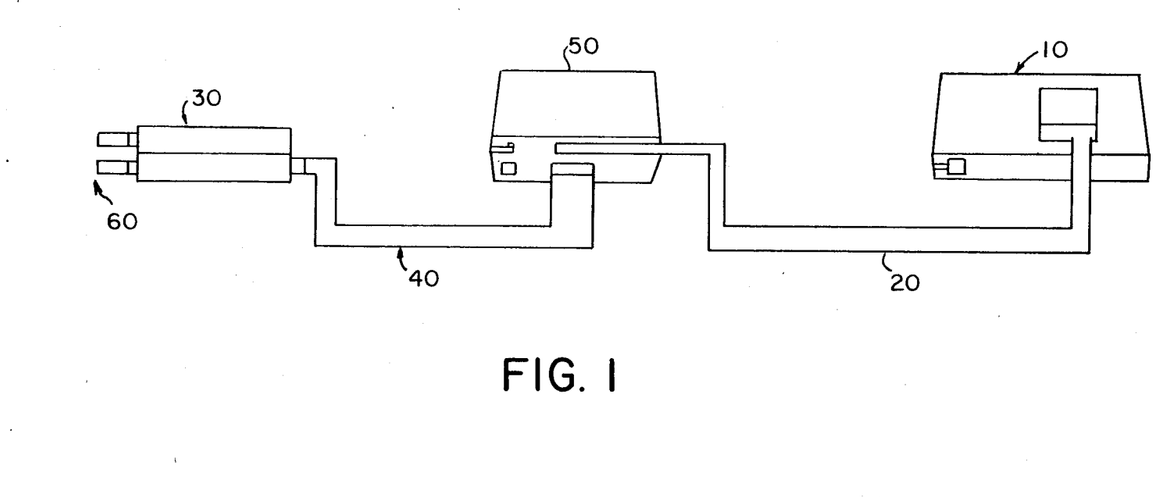
FIG. 1 is a block view of the apparatus employed in providing the combined operations of pacing and tachycardia recognition and control.

The Medtronic ® Model 2319 Custom Programmable Stimulator is a multipurpose, dual channel software programmable pulse generator. This device requires the use of the Hewlett-Packard HP-85 minicomputer 10 to write stimulation sequences using the Medtronic software language PACE and BASIC. Stimulation sequences are executed by the Model 2319 controller 50 and patient interface 30.

To use the HP-85 with the Model 2319, the following equipment must be purchased from Hewlett-Packard:
 1. HP-85A Computer—No. 85A.
 2. HP-85 16K Memory Module—No. 82903A.
 3. HP-85 ROM Drawer—No. 82936A.
 4. HP-85 Input/Output ROM—No. 00085-15003.
 5. HP-IB Interface Module—No. 82973A.

The I/O ROM is installed in the ROM drawer in one of the four slots on the back of the HP-85 minicomputer 10 as outlined in the ROM Drawer Instruction Sheet. The 16K Memory Module is installed in one of the three remaining slots. The HP-IB Interface Module is installed as outlined in the HP-IB Manual.

The HP-IB cable 20 is attached to the back of the Model 2319 Controller 50. The Medtronic ® Ribbon Cable 40 is attached to the back of the Controller 50 and then to the Patient Interface Module 30.

The Model 2319 uses the HP-85 minicomputer 10 as system controller and the Controller 50 as a Talker/Listener. The HP-IB Interface Module is preset with the following:
 Interface Select Code: 7
 HP-85 Bus Address: 21
 Controller/Noncontroller: Controller
For the Model 2319 to operate properly, these settings must be as listed above.
 The 2319 as two bus addresses:
 Major T/L: 29
 Minor T/L: 28
If other devices are used on the bus, they must have bus addresses other than 29, 28 and 21. If other devices request service by issuing SRQ, they will be ignored.

The output terminals 60, located on the Patient Interface Module 30, are designed so that no uninsulated portion of the terminal is exposed. To connect a lead to the unit, the chuck-type terminals are twisted counterclockwise. The lead connector pins are fully inserted into the ends of the terminals and secured by finger tightening each terminal while observing proper voltage polarity.

Four pairs of output terminals 60 are provided on the Model 2319 Patient Interface Module 30. They are marked PACE 1, SENSE 1, SENSE 2, PACE 2. Channel 1 is electrically isolated from Channel 2.

The sensing and stimulation functions for Channel 1 can be combined to use a single pacing lead by switching the SEPARATE/COMMON switch for Channel 1 to COMMON. If the SEPARATE/COMMON switch for Channel 1 is in the SEPARATE position, the SENSE 1 input is separated from the PACE 1 output lead and two bipolar catheters can be used. To disconnect the pacing function from the patient, the DISCONNECT/PACE switch for Channel 1 is switched to the DISCONNECT position. This position still allows sensing to occur while the pacing function is disconnected. The PACE 1 indicator lamp will still illuminate as an indicator of when a stimulus would normally occur. This switch must be in the PACE position to extend the stimulation to the patient. SENSE 2 and PACE 2 can be manipulated in the same way.

Two external interrupt inputs are provided on the back of the Controller 50. They are not electrically isolated from ground and should not be in electrical contact with the patient or other equipment which is in electrical contact with the patient. External interrupt signals must be TTL compatible, i.e. square pulse, 5 Volt amplitude and minimum pulse width of 500 μs.

These outputs are not electrically isolated from earth ground and must not be in electrical contact with the patient or other equipment which is in electrical contact with the patient.

Four trigger outputs are provided on the back of the Controll Unit 50. The trigger outputs a square waveform, 5 volts in amplitude and 1 ms in duration. These outputs are not electrically isolated from earth ground and must not be in electrical contact with the patient or other equipment which is in electrical contact with the patient.

Before the HP-85 minicomputer 10 and the Controller 50 are turned on, the two cables 20 and 40 must be connected. Patient pacing leads, external interrupts and triggers may be connected at this time, although they may be connected after power is on.

The tape cartridge must be fully inserted into the HP-85 minicomputer 10 before it is turned on. Upon turning on the HP-85 minicomputer 10 and the Controller 50, the HP-85 minicomputer 10 will automatically load and run the BASIC program "Autost" which supports the language PACE and allows pacing programs to be written. "Autost" loads "Memory" into the HP-85 active memory. This file contains up to seven Pacing programs which were in active memory the last time user executed the "Quit" command. While this is being loaded, the tape light will blink off and on and the message "BUSY" flashes on the CRT screen of minicomputer 10. If both of the cables 20 and 40 are connected and all of the hardware is working properly, the display will then indicate that the Model 2319 is in the COMMAND MODE, and will list all of the possible commands and prompt the user for a command. If one or both of the cables 20 or 40 are not properly connected or the Controller 50 is not turned on or there is a hardware failure, an appropriate message will be displayed. The Command Mode and Edit Mode may still be operational depending on the type of error. These error conditions, messages and suggested actions are summarized in Table 1 in the appended Instruction Manual.

The instructions and procedure for programming the Medtronic 2319 Custom Programmable Stimulator and the specific program employed in the practice of the present invention are appended to this application. The appended program employs both the PACE and a required BASIC program listing. The system is best explained in connection with the block diagrams shown in FIGS. 2a and 2b which depict the method and apparatus of the present invention accomplished by the hardware described above and the software appended to this application.

Figure 2A:
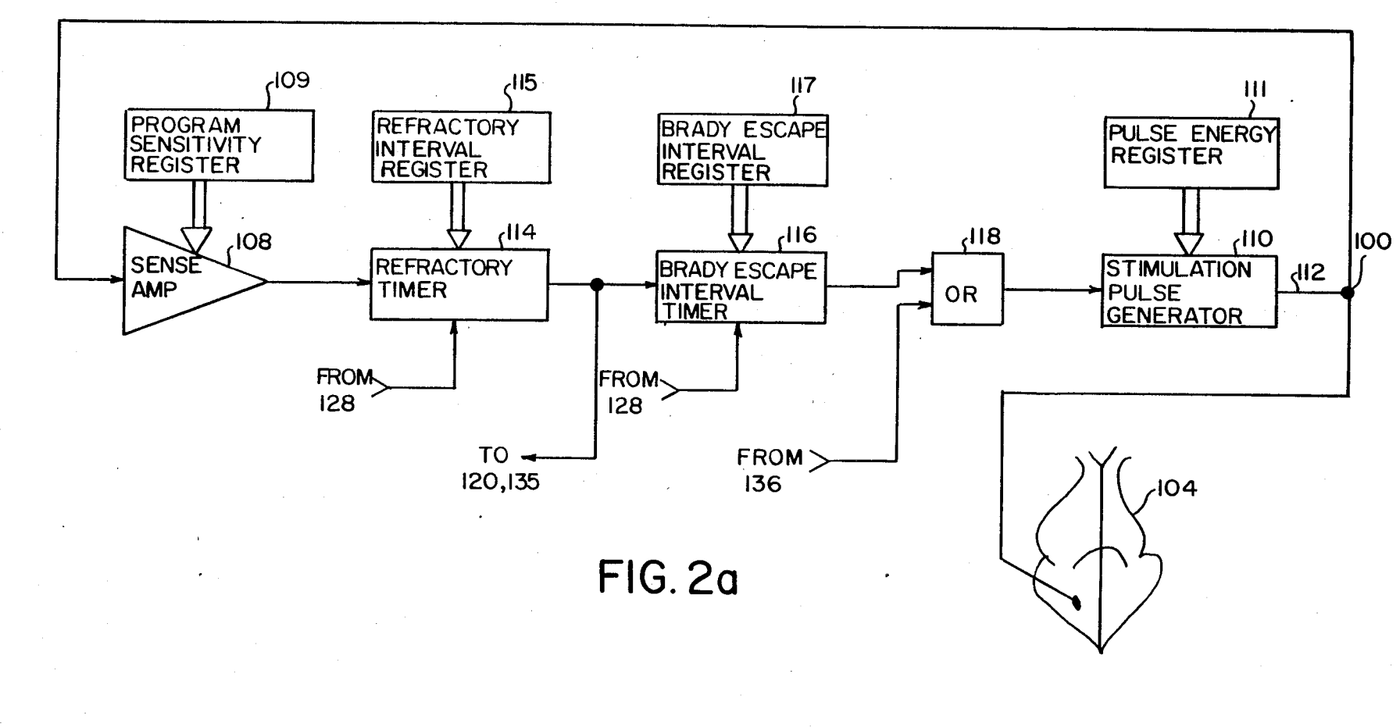
FIGS. 2a and 2b are block diagrams showing the functional arrangement of the apparatus of this invention, as well as the method of providing the combined operations of pacing and tachycardia recognition and control.

The input and output terminals 100 of the system shown in FIG. 2a are intended to be connected through standard pacing leads 102 to the ventricle of the patient's heart 104 (i.e., through a lead or leads connected to terminal 60 of FIG. 1 and to the patient's heart). The natural heart depolarization signals are conducted on conductor 106 to the input of sense amplifier 108 (in Patient Interface Module 30, FIG. 1). Stimulation pulses generated by stimulation pulse generator 110 are delivered by conductor 112 to the output terminal 100. The circuitry in between operates to determine whether a pacing stimulus should be applied in the event of bradycardia, or (in FIG. 2b) a rate scanning burst of stimuli should be delivered in the event a tachyarrhythmia is sensed and confirmed.

The output signal of the sense amplifier 108 passes through the refractory circuit 114 and the resulting SENSE signal is applied as a reset signal to the input of a brady escape interval timer 116. In the event that the escape interval timer 116 times out without an interrupting sense signal, then it applies a trigger impulse through OR gate 118 to the stimulation pulse generator 110 which responds by delivering a pacing energy stimulating pulse to the heart.

The sensitivity of the sense amplifier 108 may be adjusted or programmed by the value stored in program sensitivity register 109. Similarly, a refractory interval of the refractory timer 114 may be programmed by the value stored in program refractory interval register 115 and the brady escape interval may be programmed by the value stored in program brady escape interval register 117. The pulse energy of the stimulation pulse provided by the pulse generator 110 may be similarly programmed by the value stored in program pulse energy register 111. It will be understood that the programming of these values and intervals may be accomplished in the external equipment previously described by suitable programming instructions, but may also be programmed into implantable devices by use of the circuitry and methods disclosed in Medtronic U.S. Pat. Nos. 4,340,062, 4,379,459 and 4,401,120 embodied in the Medtronic ® Spectrax ® pacemaker.

Figure 2B:
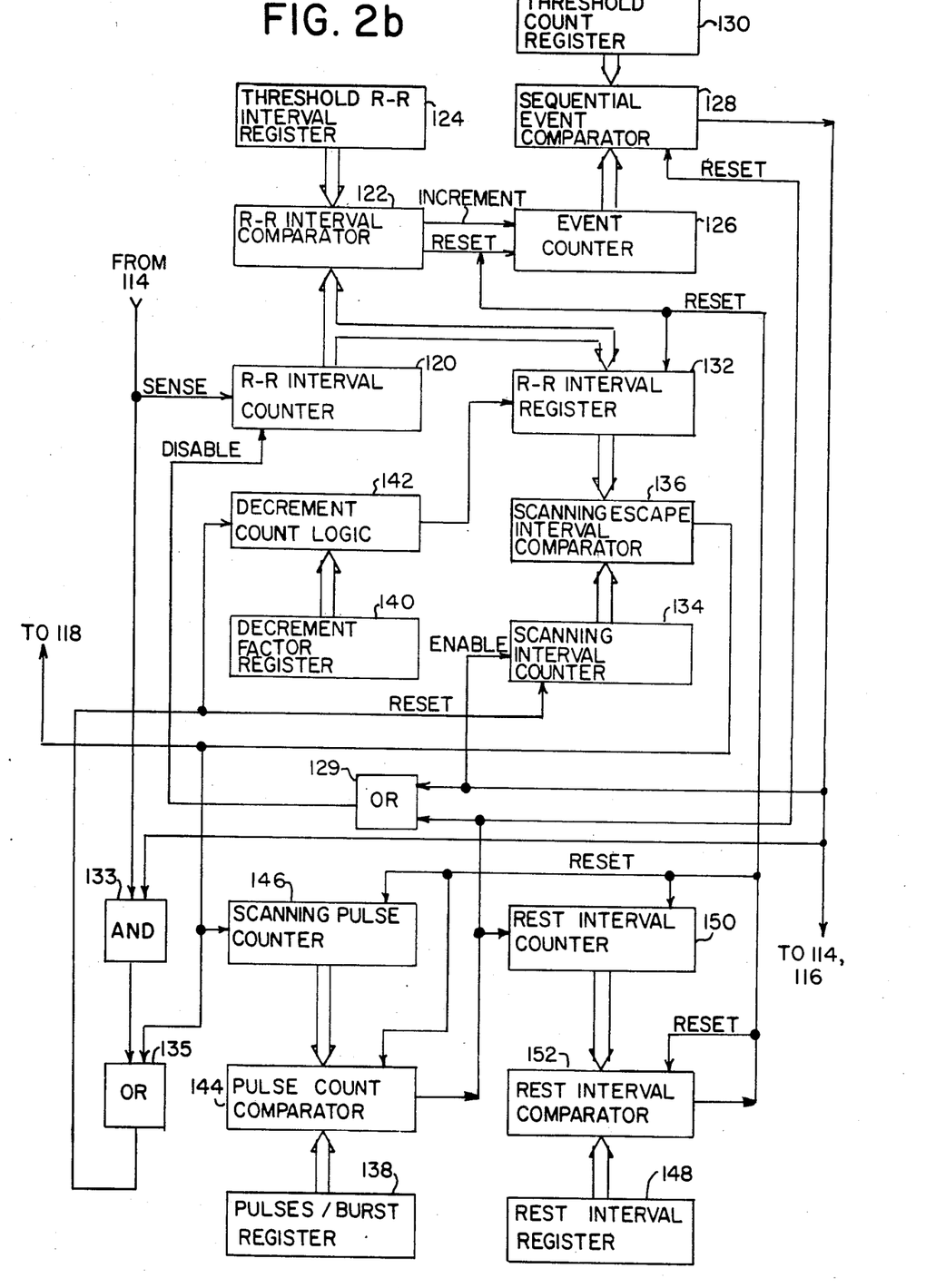

Turning now to FIG. 2b, a block diagram showing the functional arrangement of the apparatus of this invention, as well as the method of providing tachycardia recognition and control, are depicted.

FIG. 2b is intended to be connected for purpose of description to FIG. 2a by the lines entitled "from 114", "to 114", "to 116", and "to 118", etc. in a manner to be described. Very generally, the block diagram of FIG. 2b depicts the manner in which the tachycardia condition is detected and a rate scanning burst of stimulating pulses is delivered. In particular, in accordance with the present invention, the provision of SENSE signals from the ventricular sense amplifier 108 (through refractory timer 114) causes the rate scanning time interval to be reset so that natural heartbeats, particularly those originating in the ventricle, will reset the rate scanning interval and avoid the potential for fibrillation to ensue from the delivery of a competitive stimulating pulse into a vulnerable phase or zone of the heart.

A tachycardia condition is recognized and confirmed by the R-R interval counter 120, the R-R interval comparator 122, the value in program threshold interval register 124, the event counter 126, the sequential event comparator 128, and the value in the program count register 130.

The SENSE signals from the output of refractory timer 114 are applied to the R-R interval counter 120 which is reset thereby and commences to count clock pulses (not shown). The count on the R-R interval counter 120 is applied to the R-R interval comparator 122 and to the R-R interval register 132. The programmed threshold R-R interval value provided by register 124 is applied to the other inputs of the R-R interval comparator 122. The programed threshold R-R interval value may be entered in the program stored in a register in the memory of the system depicted in FIG. 1 or, in an implantable version, may be retained in a memory register through programming in the manner described in the aforementioned U.S. Patent Nos.

Each time a SENSE signal is received, it resets the count of the R-R interval counter 120. If the R-R interval counter 120 is reset prior to the time that the R-R interval comparator 122 would signal a one-to-one match between the count on counter 120 and the programed threshold R-R interval from the register 124, then an "increment" signal would be applied to the event counter 126. If, instead, the R-R interval counter 120 count reaches a count which (as a time interval) corresponds to the programmed threshold R-R interval, then the R-R interval comparator 122 would provide a reset signal to the event counter 126. If a series of sequential R-R intervals are shorter than the threshold R-R interval programmed in the register 124, then the event counter 126 will register an increasing count. If the increasing count reaches the count set in the program count register 130, then the sequential event comparator 128 will detect a match and provide an output signal to shorten the refractory interval of the refractory interval timer 114, to disable the bradycardia timer 116, to enable the scanning interval counter 134 and to disable the R-R interval counter 120 (through OR gate 129). The output signal of the sequential event comparator 128 will continue until the programmed number of pulses in the burst established by the register 138 is reached.

Thus, for example, if the threshold R-R interval register 124 were programmed to correspond to an interval of 375 ms (or 160 beats per minute), and a predetermined number, such as 5, were programmed into count register 130, and five sequential R-R intervals less than 375 ms were detected by comparators 122 and 128, then a tachyarrhythmia condition would be confirmed. The remaining elements of the block diagram of FIG. 2b would provide the programmed number of rate scanning impulses, each scanning interval being resettable by a sensed R wave, and the subsequent provision of a rest interval that would likewise be programmed.

The scanning escape interval is provided by the R-R interval register 132, the scanning interval counter 134, the scanning escape interval comparator 136, the value in program decrement factor register 140 and the decrement count register 142. Very generally, the R-R intervals that are counted by counter 120 are simultaneously applied to the register 132 so that the last R-R interval count in the sequence which was detected by sequential event comparator 128 can be used as the memory register count for the scanning escape interval. The scanning interval counter 134 is enabled by the output signal of the sequential event comparator 128 and commences to count. The scanning escape interval comparator 136 compares the count in counter 134 to the count in register 132, and when the counts match, it provides an output pulse to OR gate 118 in FIG. 2a. This output pulse passes through the OR gate 118 and triggers the stimulation pulse generator 110 into providing a stimulating pulse on the output conductor 112 to the output terminals 100 and through lead 102 through to the ventricle of patient's heart. The scanning interval counter 134 is reset through gate 135 and commences to count over again. Simultaneously, an output signal from the comparator 136 is applied to the decrement count logic 142 which decrements the count stored in the R-R interval register 132 by the value of the programmed decrement factor stored in register 140. Thus a sequence of stimulation impulses is delivered through the pulse generator 110 at decreasing intervals dependent upon the initial R-R interval corresponding to the detected R-R interval and the decrement factor which is entered into the register 140 in the manner previously described.

The number of pulses in a burst is controlled by the value in the program pulses/burst register 138, the count comparator 144 and the scanning pulse counter 146. The output pulses of the comparator 136 are applied to the counter 146 which applies the count to the comparator 144. At a second input of comparator 144, the programmed number of pulses in a burst is applied from register 138, and, when the two counts are equal, the comparator 144 provides a "start" output pulse to the rest interval timer 148. Simultaneously, a signal is applied to reset the comparator 128 and remove the ENABLE signal from the scanning interval counter 134.

The rest interval timer 148 is provided to count clock signals until its count is equal to the count or value programmed in the program rest delay register 150. The count in timer 148 is applied to one input of the count comparator 152 and the count or digital word in the register 150 is applied to a second input of the comparator 152. When both counts are equal, the comparator 152 provides a reset output signal which resets the timer 148, the count comparator 144, the event counter 126, the scanning pulse counter 146, and the R-R interval register 132. The count in comparator 152 is also simultaneously reset. The program rest delay interval may be set for as long a delay as desired and prevents the pulse generator from providing a further rate scanning burst to the patient's heart for that interval of time. As noted earlier, the output signal of the sequential event comparator 128 has been applied to reset the refractory interval 114 and disable the bradycardia timer 116 for the entire interval of the rate scanning burst. The R-R interval counter 120 is disabled for the entire interval of the rate scanning burst and the rest delay interval by the DISABLE signal applied through OR gate 129.

The circuit of FIG. 2b as described operates in an asynchronous fashion and is suitable for use in the treatment of paroxysmal supra-ventricular tachycardia episodes or atrial tachycardia. The previously decremented R-R interval could be retained in the R-R interval register 132 by not resetting R-R interval register 132 and used as the initial interval in the next rate scanning cycle, if desired.

Turning now to the use of the method and apparatus of the present invention for the treatment of ventricular tachycardias, and again in reference to FIG. 2b, the sense signal from the refractory timer 114 is also applied through OR gate 135 to the reset input of the scanning interval counter 134. During the rate scanning burst, the refractory interval is forshortened from its normal refractory interval to a proportionally smaller interval that may be programmed in dependence on the characteristics of the PQRST waveform in the particular patient at the tachycardia threshold rate. Therefore, SENSE signals occurring after the end of the refractory interval but before the timing out of the scanning interval may be applied to the OR gate 135 to reset the scanning interval in the event that the ventricle does contract spontaneously during the delivery of the burst of rate scanning impulses. In this fashion, the delivery of a stimulating impulse into a dangerous or vulnerable zone of the heart may be avoided.

Since the SENSE signals should only be provided to the decrement count logic 142 and to reset the scanning interval counter 134 after tachycardia is confirmed and during the delivery of the burst of stimuli, an AND gate 133 is provided to direct the SENSE signals through OR gate 135 only while the comparator 128 provides an output signal.

Although FIG. 2b shows that the R-R interval is measured to confirm tachycardia, the invention contemplates the confirmation of tachycardia by any of the known techniques, including the rate-of-change of successive R waves (see for example, the description in U.S. Ser. No. 577,631 filed Feb. 6, 1984 and commonly assigned). In addition, the invention contemplates an initial scanning stimulation interval that is shorter or longer than the preceding measured R-R interval and may be independent from the measured R-R interval.

The language PACE has been specially designed for the creation of stimulation sequences. It allows the user to write his own programs by placing together a number of instructions in a logical way in order to get the desired protocol. There are 33 different instructions. For example, one instruction outputs a pacing pulse, another provides a delay or interval, another turns on the sense amplifier and yet another enables a tachycardia detection scheme. The instructions are placed in order and then executed from top to bottom. For example, the following instruction outputs a constant current pulse on Channel 2 with 4 mA amplitude and 1.2 ms pulse width:

| 1. Pulse/CC | |
|---|---|
| a. Channel | 2 |
| b. Amplitude | 4 mA |
| c. Pulse Width | 1.2 ms |

Alone it is not very useful, but if a delay is added:

| 1. DELAY | |
|---|---|
| a. Delay | 850 ms |
| 2. PULSE/CC | |
| a. Channel | 2 |
| b. Amplitude | 4 mA |
| c. Pulse Width | 1.2 ms |

Execution would begin with No. 1, the DELAY instruction. The unit delays for 850 ms. After this time, execution continues with No. 2, the PULSE instruction, and outputs a pulse on Channel 2. This program is not allowable since the Controller cannot determine what to do after the PULSE instruction. A HALT instruction added as the last instruction would correct this situation.

| 1. DELAY | |
|---|---|
| a. Delay | 850 ms |
| 2. PULSE/CC | |
| a. Channel | 2 |
| b. Amplitude | 4 mA |
| c. Pulse Width | 1.2 ms |
| 3. HALT | |

Execution would begin with No. 1, the DELAY, then continue with No. 2, the PULSE and then execute the HALT instruction which tells the device to stop execution. This is a legal program but results in only a single pulse. If the HALT is replaced with a GOTO, a "Loop" will be set up:

| 1. DELAY | |
|---|---|
| a. Delay | 850 ms |
| 2. PULSE/CC | |
| a. Channel | 2 |
| b. Amplitude | 4 mA |
| c. Pulse Width | 1.2 ms |
| 3. GOTO | |
| a. Instruction | 1 |

Execution begins with the DELAY, then continues with the PULSE. Then No. 3 is executed which instructs the device to GOTO Instruction No. 1 in the sequence, and begin execution with No. 1 again. This is known as a "Branch" because it causes the device to jump out of its normal execution sequence and execute the "branch instruction." This is a simple program that executes a DELAY, a PULSE, a DELAY, and a PULSE indefinitely i.e., asynchronous pacing with a cycle length of 850 ms.

To create demand pacing from the above sequence, it would be necessary for the device to begin the DELAY instruction every time a sensed depolarization occurs. Adding a single instruction accomplishes this:

| 1. ON SENSE GOTO | |
|---|---|
| a. Channel | 2 |
| b. Instruction | 2 |
| c. # Senses | 1 |
| d. Sensitivity | 2.5 mV |
| e. Type of Jump | 0 |
| 0 = Immediate Jump and 1 = Delayed Jump | |
| 2. DELAY | |
| a. Delay | 850 ms |
| 3. PULSE/CC | |
| a. Channel | 2 |
| b. Amplitude | 4 mA |
| c. Pulse Width | 1.2 ms |
| 4. GOTO | |
| a. Instruction | 2 |

Execution begins with No. 1 which turns on the sense amplifier on Channel 2 with a sensitivity of 2.5 mV. It specifies that when a sense occurs, execution is to be interrupted immediately and begin again with Instruction No. 2. In the absence of a sense, No. 2 is completed, then in turn No. 3, the PULSE, and then No. 4, the GOTO. Only when 850 ms pass without a sense will the PULSE instruction be executed. This is VVI or AAI pacing, depending on catheter location, without refractory.

To create VVT or AAT from the above sequence, just change the Branch Instruction No. of the ON SENSE Instruction:

| 1. | ON SENSE GOTO | |
|---|---|---|
| | a. Channel | 2 |
| | b. Instruction | 3 |
| | c. # Senses | 1 |
| | d. Sensitivity | 2.5 mV |
| | e. Type of Jump | 0 |
| | 0 = Immediate Jump and 1 = Delayed Jump | |
| 2. | DELAY | |
| | a. Delay | 850 ms |
| 3. | PULSE/CC | |
| | a. Channel | 2 |
| | b. Amplitude | 4 mA |
| | c. Pulse Width | 1.2 ms |
| 4. | GOTO | |
| | a. Instruction | 2 |

In this case, whenever a sensed depolarization occurs, execution branches to No. 3 which outputs a PULSE. Thus, in the presence of spontaneous activity of cycle length less than 850 ms, PULSES will be delivered into the QRS complex. If the cycle length of the spontaneous activity becomes greater than 850 ms, PULSES will be delivered. Note that this simple program has no software upper rate limit. (The program will have a hardware upper rate limit bounded by the sense amplifier blanking.)

Instructions

The ON SENSE instruction is called a "Conditional Branch" type of instruction because if the given condition is met, program execution branches to the specified instruction. All of the 33 instructions have been conceptually grouped into five groups: PULSE GROUP, PROGRAM CONTROL GROUP, DELAY GROUP, CONDITIONAL BRANCH GROUP, AND OTHER.

1. PULSE GROUP

Each of the six instructions in this group output a pacing pulse. PULSE/CC outputs a pulse of constant current. PULSE/CV outputs a pulse of "constant voltage" (constant peak voltage). There are two instructions that automatically increment or decrement amplitude and/or pulse width with each execution. One is a constant current type and one is a constant voltage type. There are two instructions that allow incrementing and decrementing of amplitude and/or pulse width manually using the Special function keys of the HP-85. Thus, these parameters may be altered during program execution. One is a constant current type and one is a constant voltage type. The minimum pulse interval is 80 ms.

2. PROGRAM CONTROL GROUP

There are three instructions in this group. GOTO which causes a branch when executed and HALT which stops program execution have been used in previous examples. PAUSE suspends program execution until resumed by the user. This is done by pressing the RESUME key on the Digital Control Unit keyboard. It should be noted that PAUSE and HALT keys are also on the keyboard and have the same effect as the PAUSE and HALT instructions.

3. DELAY GROUP

There are five instructions in this group, and they all cause a delay for the specified amount of time. DELAY has been used in previous examples. There is also a version that automatically increments or decrements the delay value with a user programmable number of executions. There is another version that allows incrementing and decrementing of the delay value manually using the Special Function keys of the HP-85. Another delay instruction calculates the delay value as the specified percentage of the last measured interval of a tachycardia. This instruction can be used to adapt a pacing rate to a spontaneous rate. For long delays, on the order of minutes, the WAIT instruction can be used.

4. CONDITIONAL BRANCH GROUP

There are eight instructions which set up conditions which cause a branch in program execution. There are five more instructions for disabling or turning off these conditions. Together, these thirteen instructions make up the conditional branch group. Simple pacing protocols may be written using only instructions from the previous three groups. But instructions in this group make the device powerful. ON SENSE has already been used in previous examples. Another version of ON SENSE allows incrementing and decrementing of the sensitivity manually using the Special Function keys of the HP-85. OFF SENSE turns off the sense amplifier. ON TIME sets up a hardware timer which causes a branch when it times out. By using this instruction with a DELAY, two independent timeouts can be set simultaneously. OFF TIME turns off the hardware timer. ON TACHYCARDIA allows a branch in program execution if a tachycardia is detected. The user defines the tachycardia using rate acceleration, trigger interval and number of intervals. OFF TACHYCARDIA disables the tachycardia detection scheme. ON EXTERNAL INTERRUPT allows a program branch when an interrupt from another device occurs. In this way, program execution may be altered by inputs from another device. OFF EXTERNAL INTERRUPT disables this feature. IF COUNT sets up a counter and every time the instruction is executed, the counter is incremented. When the counter reaches the specified limit, a program branch occurs. ON MANUAL INTERRUPT allows a program branch when the specified manual interrupt key on the Digital Control Unit keyboard is pressed. Thus, the user can alter program execution manually. OFF MANUAL INTERRUPT disables this feature. IF CONDITION allows a program hranch when program execution executes the instruction and the correct switch is turned on.

5. OTHER

There are six instructions which do not fit into the first four groups. The first is SEND TRIGGER which sends a trigger of "Sync" pulse to another device. This can be used to trigger oscilloscopes and strip chart recorders as well as other devices. These triggers are not electrically isolated and must not be connected to patient leads.

The second instruction is SEND INTERRUPT. This is a special instruction to be used only when the 2319 has a program downloaded to it and the HP-85 is executing a user generated controlling program. This instruction sends an interrupt number which must be acknowledged and decoded by user software.

The third, fourth, fifth and sixth instructions are related. The CHANGE COUNT instruction allows changing the running count of the IF COUNT instruction. The RESET DELAY with AUTO ADJUST, RESET PULSE WITH AUTO ADJUST/CV and RESET PULSE WITH AUTO ADJUST/CC reset varying auto adjust parameters to initial values.

Parameters

In the example programs, several parameters were associated with each instruction. These parameters may be programmed or "specified" at the time the program is written. If not specified, nominal values are assigned. They may also be modified at any time the program is being edited. It is possible to alter some parameters manually during execution, such as pulse amplitude, pulse width, sensitivity and delay values. It is not possible to edit a program during execution. When modifying a parameter, the allowed range for that parameter is displayed and the user is prompted for the new value.

This concludes the introduction to the device and the language PACE. Each of the instructions will be described in detail, with examples, in a later section. The next section will discuss how to create, modify and manipulate programs, select a program for execution and execute a program.

OPERATING INSTRUCTIONS

In order to create a program for execution, the user must become familiar with a small set of commands (not the same as instructions). Their purpose is to create programs and move them to and from tape if desired. The user can have up to seven separate programs in HP-85 memory (and, thus, readily accessible for execution) at any time. He may store many more on tape as he writes them. The commands have been divided into four groups or "Modes". There is a "COMMAND MODE" which is used for tape manipulation and an "EDIT MODE" which is used for program creation and modification. There is also a "SELECTION MODE" in which the user can select a program for execution, and there is the "ACTIVATION MODE" in which a program is actually executed. A typical sequence would be EDIT, SELECT and ACTIVATE. When the HP-85 is powered on, the 2319 is automatically in COMMAND MODE.

The following program listing entitled "VVI PACING WITH TACHYCARDIA DETECTION PROGRAM" follows the above instructions except as noted therein. The program accomplishes most of the functions described in connection with FIGS. 2a and 2b except for the rest interval function (blocks 148, 150, 152) which was not programmed due to anticipated operator presence while the system is in use. In addition, the program contemplates possible interrupts which are not described in regard to the FIG. 2a and 2b diagrams, again due to anticipated user control.

Finally the present invention is described in conjunction with an external diagnostic and pacing system. It is apparent that it could be implemented in a fully implantable pacemaker employing either digital logic circuitry or a programmed microprocessor based system or a combination of both technologies.

VVI PACING WITH TACHYCARDIA DETECTION PROGRAM

This program will VVI pace at a preset rate, continuously monitoring sensed rate for tachycardia detection. The rate acceleration parameter for the tachycardia statement may be activated. Once a tachycardia is detected, VVI pacing at the detected tachycardia cycle length occurs, decreasing by 1 millisecond each cycle.

The following parameters are adjustable from the keyboard during program execution: Tachycardia trigger interval, number of intervals necessary to trigger a tachycardia, basic VVI pacing cycle length and the number of 1-msecond VVI pacing decrements during tachycardia therapy. Following the accelerated VVI pacing, the program returns to the start and VVI paces with tachycardia detection. The program will deliver 3 therapies automatically when MANUAL INTERRUPT KEY 1 is pressed, then MANUAL INTERRUPT KEY 1 must be pressed to reenable the tachycardia detection.

It is not possible to implement this program using the Medtronic PACE program. A custom basic program was written to allow more elaborate interactions between the 2319 stimulator and the HP-85 computer. The PACE program XTY4 contains many more parameters which can be adjusted or changed. The user may permanently change a parameter by editing the XTY4 program using the Medtronic PACE program and restoring the XTY4 program on the VVI PACING WITH TACHYCARDIA DETECTION tape. Additional software would be neccessary to add parameter changes during execution. The additional information will outline the different program displays.

1. The VVI PACING WITH TACHYCARDIA DETECTION tape is inserted into the computer and turned on.

PRESS K1 TO DOWNLOAD

2. Press K1 on the computer to load the pacing protocol in the 2319 stimulator.

3. Once the program is loaded, the following display occurs. The user now presses the START key on the 2319.

PRESS START

4. The following display comes up during execution. Eight variables may be altered by pressing K2. Eight parameters are displayed: The tachycardia trigger interval, the number of intervals necessary to recognize tachycardia, the basic VVI cycle length, the number of decrements in the VVI cycle length starting at tachycardia cycle length, sensitivity, pulse width, the auto decrement value for tachy therapy and tachycardia detection rate acceleration.

| EXECUTING | |
|---|---|
| PRESS K2 TO ENTER NEW PARAMETER VALUE | |
| TINTms | # INTS |
| 500 | 6 |
| VVI CL ms | COUNT |
| 850 | 25 |
| SENmv | PWms |
| 2.5 | 1 |
| DECms | ACCELms |
| 1 | 0 |

5. When K2 is pressed, the soft key labels appear and the user selects the appropriate parameter to change by pressing a soft key again. K1 selects the tachycardia trigger interval, K2 the number of intervals to trigger tachycardia recognition, K3 selects the basic VVI pacing rate, K4 selects the number of 1-msec decrements in the VVI cycle length starting at a VVI cycle length equal to the detected tachycardia cycle length, K5 selects sensitivity, K6 pulse width, K7 decrements in msec and K8 tachycardia detection rate acceleration.

```
 EXECUTING
PRESS K2 TO ENTER NEW PARAMETER VALUE
 TINTms                    # INTS
  500                        6
 VVI CL ms                 COUNT
  850                       25
 SENmv                     PWms
  2.5                        1
 DECms                     ACCELms
  1                          0
 SEN      PW       DECMS      ACCEL
 TINT     #INT     VVI CL     CNT
```

6. If the user presses K1, a prompt statement is displayed. A new value is entered and the user pressed the END LINE key. Note the entered value must be a number and the user determines if it is an appropriate value. Entering a non-numeric entry will abort the program and require a total restart.

```
ENTER NEW 1 TACHYCARDIA TRIGGER INTERVAL
?
```

7. The display will now return to executing (Step 4). The following is a listing of the PACE program and the required BASIC program:

| Program XTY4 | | |
|---|---|---|
| (21 instructions) | | |
| 1. ON MANUAL INTERRUPT GOTO | | |
| (a) Man. Interrupt | 1 | |
| (b) Instruction | 20 | |
| (c) Type of jump | 0 | |
| 0 = Immediate jump and 1 = Delayed jump | | |
| 2. GOTO | | |
| (a) Instruction | 5 | |
| 3. ON TACHYCARDIA GOTO | | |
| (a) Channel | 2 | |
| (b) Instruction | 9 | |
| (c) Rate Accel | 0 | ms/int. |
| (d) Min. Interval | 500 | ms |
| (e) # Intervals | 6 | |
| (f) Sensitivity | 2.5 | mV |
| 4. START TIMER | | |
| 5. ON SENSE GOTO | | |
| (a) Channel | 2 | |
| (b) Instruction | 4 | |
| (c) # Senses | 1 | |
| (d) Sensitivity | 2.5 | mV |
| (e) Type of jump | 0 | |
| 0 = Immediate jump and 1 = Delayed jump | | |
| 6. DELAY WITH MANUAL ADJUST | | |
| (a) Delay | 850 | ms |
| (b) ΔDelay | 15 | ms |
| (c) Lower Bound | 150 | ms |
| (d) Upper Bound | 1500 | ms |
| (e) Adjust Key | 1 | |
| 7. PULSE/CV | | |
| (a) Channel | 2 | |
| (b) Amplitude | 5 | V |
| (c) Pulse Width | 1 | ms |
| 8. GOTO | | |
| (a) Instruction | 5 | |
| 9. OFF TACHYCARDIA | | |
| (a) Channel | 2 | |
| 10. READ TIMER | | |
| (a) Interrupt | 117 | |
| 11. ON SENSE GOTO | | |
| (a) Channel | 2 | |
| (b) Instruction | 12 | |

| Program XTY4 | | |
|---|---|---|
| (21 instructions) -continued | | |
| (c) # Senses | 1 | |
| (d) Sensitivity | 0 | mV |
| (e) Type of jump | 0 | |
| 0 = Immediate jump and 1 = Delayed jump | | |
| 12. DELAY WITH AUTO ADJUST | | |
| (a) Delay | 850 | ms |
| (b) Auto-Increment | −1 | ms |
| (c) Boundary | 100 | ms |
| (d) Count | 0 | |
| 13. IF COUNT GOTO | | |
| (a) Count | 26 | |
| (b) Instruction | 16 | |
| 14. PULSE/CV | | |
| (a) Channel | 2 | |
| (b) Amplitude | 5 | V |
| (c) Pulse Width | 1 | ms |
| 15. GOTO | | |
| (a) Instruction | 11 | |
| 16. IF COUNT GOTO | | |
| (a) Count | 3 | |
| (b) Instruction | 18 | |
| 17. GOTO | | |
| (a) Instruction | 20 | |
| 18. RESET DAA | | |
| (a) Instruction | 12 | |
| 19. GOTO | | |
| (a) Instruction | 4 | |
| 20. RESET DAA | | |
| (a) Instruction | 12 | |
| 21. GOTO | | |
| (a) Instruction | 3 | |

```
1   CLEAR & ENABLE KBO 33
2   !
3   ! THIS PROGRAM DETECTS A
4   ! TACHYCARDIA AND THEN VVI
5   ! PACES STARTING AT A CYCLE
6   ! LENGTH = TO TACHY CL. THE CL
7   ! IS DECREMENTED IN MS UNTIL
8   ! A COUNT # OF CYCLES OCCURS
9   !
10  INTEGER L,X,Y,F1,Z,E,(20,9) T,
    Q,B,H,N1,H4
11  Q=0 & F1=0 & D1=500 & D2=6 &
    D3=850 & D4=26 & D5=20 & D6 =100 &
    D7=−1 & D8=0
13  SHORT H2,G2
14  H2=128
15  ! XTY IS THE PACE PROTOCOL
16  !
20  ASSIGN# 1 TO "XTY4"
25  !
26  ! THIS SECTION LOADS THE XTY
27  ! PROGRAM INTO THE E ARRAY
28  !
30  READ# 1; L
40  FOR X=1 TO L
50  Y=X−1
60  IF Y=L−1 THEN E(Y,0)=01 & GO TO 80
70  E(Y,O)=X
80  FOR Z=1 TO 9
90  READ# 1; E(Y,Z)
100 NEXT Z
110 NEXT X
130 ON INTR 7 GOSUB 500
140 ENABLE INTR 7; 8
141 CLEAR
150 DISP "PRESS K1 TO DOWNLOAD"
160 ON KEY# 1 GOTO 230
170 GOTO 170
180 !
181 !
182 ! LINES 230 TO 261 DOWNLOAD
183 ! THE XTY PROGRAM TO THE
```

```
184 ! 2319 STIMULATOR
185 ! 230 SEND 7; MTA LISTEN 28 DATA 9
186 !
230 OUTPUT 729 USING "#,W"; L &
232 T=0 & Q=L
240 FOR X=1 TO 9 & IF E(T,X)=999
    99 THEN GOTO 260
250 OUTPUT 729 USING "#,W"; E(T,
    X) & Q=Q+E(T,X) & NEXT X
260 T=E(T,O) & IF T#-1 THEN GOTO
    240
261 OUTPUT 729 USING "#,B"; Q &
    SEND 7; MTA LISTEN 28 DATA
    8
262 CLEAR
263 DISP "PRESS START"
265 GOTO 265
300 !
301 !
302 ! THE SUBROUTINE AT LINE 500
303 ! HANDLES INTERRUPTS
308 !
309 !
314 !
315 !
500 STATUS 7,1; X & G=SPOLL(729)
501 IF G=117 THEN ENTER 728 USIN
    G "#,W"; H ELSE GOTO 506
502 SEND 7; MTA LISTEN 28 DATA
    10
503 OUTPUT 729 USING "#,B"; 144
504 OUTPUT 729 USING "#,B"; 112
505 OUTPUT 729 USING "#,W"; H
506 IF G=66 THEN GOSUB 600
507 IF G=72 THEN CLEAR & DISP "P
    RESS K1 TO DOWNLOAD" 8 OFF K
    EY# 2 & ON KEY# 1 GOTO 230 &
    GOSUB 1200
508 ENABLE INTR 7;8
510 RETURN
550 !
551 !
557 !
600 CLEAR & DISP "EXECUTING"
601 DISP "PRESS K2 TO ENTER NEW
    PARAMETER VALUE"
602 ON KEY# 2 GOSUB 800 & GOSUB
    1000 & RETURN
800 ON KEY# 1, "TINT" GOSUB 850
801 ON KEY# 2, "#INT" GOSUB 870
802 ON KEY# 3, "VVI CL" GOSUB 890
803 ON KEY# 4, "CNT" GOSUB 900
804 ON KEY# 5, "SEN" GOSUB 1300
805 ON KEY# 6, "PW" GOSUB 1320
806 ON KEY# 7, "DECMS" GOSUB 1340
807 ON KEY# 8, "ACCEL" GOSUB 1360
808 KEY LABEL
809 RETURN
850 CLEAR 7 DISP "ENTER NEW TACH
    YCARDIA TRIGGER INTERVAL" &
    INPUT G1 & Z=O & GOSUB 910
851 Z=12 & GOSUB 910 & D1=G1 & G
    OSUB 600 & RETURN
870 CLEAR & DISP "ENTER NEW NUMB
    ER OF INTERVALS TO TRIGGER"
    & INPUT G1 & Z=1 & GOSUB 910
871 Z=13 & GOSUB 910 & D2=G1 & G
    OSUB 600 & RETURN
890 CLEAR & DISP "ENTER NEW VVI
    CYCLE LENGTH" & INPUT G1 & Z=
    2 & GOSUB 910
891 D3=G1 & GOSUB 600 & RETURN
900 CLEAR & DISP "ENTER NEW # OF
    DECREMENTS" & INPUT G1 & G1=
    G1+1 & Z=3 & GOSUB 910
901 D4=G1 & GOSUB 600 & RETURN
910 IF Z=0 THEN Z1=21 & Z2=151 &
    GOTO 950
912 IF Z=12 THEN Z1=28 & Z2=144
    & GOTO 950
913 IF Z=13 THEN Z1=31 & Z2=144
    & GOTO 970
920 IF Z=1 THEN Z1=20 & Z2=151 &
    GOTO 970
930 IF Z=2 THEN Z1=56 & Z2=144 &
    GOTO 950
934 IF Z=3 THEN Z1=125 & Z2=144
    & GOTO 950
936 IF Z=4 THEN Z1=33 & Z2=144 &
    GOTO 970
938 IF Z=5 THEN Z1=49 & Z2=144 &
    GOTO 970
940 IF Z=6 THEN Z1=75 & Z2=144 &
    GOTO 970
942 IF Z=7 THEN Z1=137 & Z2=144
    & GOTO 970
944 IF Z=8 THEN Z1=114 & Z2=144
    & GOTO 950
945 IF Z=9 THEN Z1=26 & Z2=144 &
    GOTO 950
946 IF Z=10 THEN Z1=27 & Z2=151
    & GOTO 950
947 IF Z=11 THEN Z1=105 & Z2=144
    & GOTO 950
950 SEND 7; MTA LISTEN 28 DATA
    10
952 OUTPUT 729 USING "#,B"; Z2
953 OUTPUT 729 USING "#,B"; Z1
954 OUTPUT 729 USING "#,W"; G1
960 GOSUB 1100
961 RETURN
970 SEND 7; MTA LISTEN 28 DATA 11
971 OUTPUT 729 USING "#,B", Z2
973 OUTPUT 729 USING "#,B"; Z1
974 OUTPUT 729 USING "#,B"; G1
975 GOSUB 1100 & RETURN
1000 DISP & DISP & DISP "TINTms";
    TAB(18); "# INTS"
1001 DISP D1;TAB(18);02
1002 DISP "VVI CL ms";TAB(18); "COUNT"
1003 DISP D3;TAB(18);D4—1
1004 DISP "SENmv";TAB(18);"PWms"
1005 DISP D5*.125;TAB(18);D6*.01
1006 DISP "DECms";TAB(18);'ACCELms"
1007 DISP —D7;TAB(18);08
1008 RETURN
1100 OFF KEY# 1 & OFF KEY# 2 &
    OFF KEY#3 & OFF KEY# 4
1105 RETURN
1200 D1=500 & D2=6 & D3=850 & D4=26
    & D5=20 & D6=100 & D7=—1 &
    D8=0 & RETURN
1300 CLEAR & DISP "ENTER NEW SENSITIVITY
    VALUE IN MV" & INPUT G2 & G1=G2/
    .125 & Z=4 & GOSUB 910 & Z=5
1301 GOSUB 910 & Z=11 & GOSUB 910 &
    D5—G1 & GOSUB 600 & RETURN
1320 CLEAR & DISP "ENTER NEW PULSE
    WIDTH" & INPUT G2 & G1=G2/
    .01 & Z=6 & GOSUB 910 & Z=7 &
    GOSUB 910
1321 D6=G1 & GOSUB 600 & RETURN
1340 CLEAR & DISP "ENTER NEW TACHYCARDIA
    DECREMENT VALUE IN MS" & INPUT
    G1 & G1=—G1 & Z=8 & GOSUB 910
1341 D7=G1 & GOSUB 600 & RETURN
1360 CLEAR & DISP "ENTER NEW TACHYCARDIA
    ACCELERATION" & INPUT G1 &
    Z=9 & GOSUB 910 & Z=10 &
    GOSUB 910
1361 D8=G1 & GOSUB 600 & RETURN
8000 END
```

When a parameter is changed in the PACE program file and stored on tape, the initial display value in the BASIC program must be updated. Line 11 of the BASIC program initializes the display values which are stored in variables D1 to D8. The variables correspond to the parameters as follows:

D1—Tachycardia trigger interval
D2—#of intervals

D3—VVI cycle length
D4—Tachycardia therapy count
D5—Sensitivity
D6—Pulse width
D7—Decrement
D8—Acceleration Certain parameters must be divided by a division constant before they are stored in the variable. When changing the initial parameter value for the following parameters, the corresponding division constant must be used:

Pulse Amplitude (V): 0.05
Pulse Width (ms): 0.01
Sensitivity (mV): 0.125

For example, a new initial sensitivity value of 1 mV would be equal to 1/0.125 and stored in D5.

Although the invention has been described with reference to a particular embodiment, it is to be understood that this embodiment is merely illustrative of the appliction of the principles of the invention. Numerous modifications may be made therein and other arrangements may be devised without departing from the spirit and scope of the invention.

What is claimed is:

1. The method of controlling a tachycardia condition comprising the steps of:
   (a) sensing natural heart depolarizations and providing sense signals in response thereto;
   (b) confirming a tachycardia condition;
   (c) generating a burst of a plurality of spaced heart stimulating pulses which potentially allow tachycardia to be terminated;
   (d) establishing escape intervals between each of said plurality of spaced heart stimulating pulses; and
   (e) restarting an escape interval in the event that a sense signal is provided during an escape interval in response to a natural heart depolarization during the provision of said burst of heart stimulating pulses, whereby the provision of a stimulating pulse in the vulnerable phase of the heart cycle is avoided.

2. The method of claim 1 further comprising the step of:
   varying the successive escape intervals between successive stimulating pulses in the burst in a predetermined pattern upon the generation of each heart stimulating pulse in the burst and upon the restarting of an escape interval in response to a sense signal.

3. The method of claim 2 wherein said step of varying the escape interval comprises shortening each successive escape interval by a predetermined decrement factor.

4. The method of any of the claims 1-3 wherein the step of establishing escape intervals further comprises:
   (a) measuring the tachycardia intervals between successive natural heartbeats;
   (b) storing the measured intervals; and
   (c) employing the measured interval as the initial escape interval.

5. The method of any of the claims 1-3 wherein the step of confirming a tachycardia further comprises:
   (a) measuring the intervals between successive natural heartbeats against an established threshold beat-to-beat tachycardia value;
   (b) counting each measured interval that is shorter than said threshold value; and
   (c) confirming the presence of tachycardia when the count of measured intervals shorter than said threshold value exceeds an established count value.

6. The method of any of the claims 1-3 wherein:
   the step of establishing escape intervals further comprises:
   (a) measuring the tachycardia intervals between successive natural heartbeats;
   (b) storing the measured intervals;
   (c) employing the measured interval as the initial escape interval; and
   wherein the step of confirming a tachycardia further comprises:
   (a) measuring the intervals between successive natural heartbeats against an established threshold beat-to-beat tachycardia value;
   (b) counting each measured interval that is shorter than said threshold value; and
   (c) confirming the presence of tachycardia when the count of measured intervals shorter than said threshold value exceeds an established count value.

7. The apparatus for controlling a tachycardia condition comprising:
   (a) means for sensing natural heart depolarizations and providing sense signals in response thereto;
   (b) means for confirming a tachycardia condition;
   (c) means for generating a burst of a plurality of spaced heart stimulating pulses which potentially allow tachycardia to be terminated;
   (d) means for establishing escape intervals between each of said plurality of spaced heart stimulating pulses; and
   (e) means for restarting an escape interval in the event that a sense signal is provided during an escape interval in response to a natural heart depolarization during the provision of said burst of heart stimulating pulses, whereby the provision of a stimulating pulse in the vulnerable phase of the heart cycle is avoided.

8. The apparatus of claim 7 further comprising means for varying the escape intervals between successive stimulating pulses in the burst in a predetermined pattern upon the generation of each heart stimulating pulse in the burst and upon the restarting of an escape interval in response to a sense signal.

9. The apparatus of claim 7 wherein said means for varying the escape interval comprises means for shortening each successive escape interval by a predetermined decrement factor.

10. The apparatus for any of the claims 7-9 the means for establishing escape intervals further comprises:
    (a) means for measuring the tachycardia intervals between successive natural heartbeats;
    (b) means for storing the measured intervals; and
    (c) means for employing the measured interval as the initial escape interval.

11. The apparatus for any of the claims 7-9 wherein the means for confirming a tachycardia further comprises:
    (a) means for measuring the intervals between successive natural heartbeats against an established threshold beat-to-beat tachycardia value;
    (b) means for counting each measured interval that is shorter than said threshold value; and
    (c) means for confirming the presence of tachycardia when the count of measured intervals shorter than said threshold value exceeds an established count value.

12. The apparatus of any of the claims 7-9 wherein the means for establishing escape intervals further comprises:
(a) means for measuring the tachycardia intervals between successive natural heartbeats;
(b) means for storing the measured intervals; and
(c) means for employing the measured interval as the initial escape interval; and wherein the means for confirming a tachycardia further comprises:
(a) means for measuring the intervals between successive natural heartbeats against an established threshold beat-to-beat tachycardia value;
(b) means for counting each measured interval that is shorter than said threshold value; and
(c) means for confirming the presence of tachycardia when the count of measured intervals shorter than said threshold value exceeds an established count value.

13. The method of detecting and treating a tachycardia condition comprising the steps of:
(a) sensing natural heart depolarizations and providing sense signals in response thereto;
(b) measuring the intervals between successive sense signals and confirming tachycardia as a function of the measured intervals;
(c) in response to a confirmed tachycardia, generating a stimulating pulse at the end of a first escape interval measured from a preceding sense signal and applying the pulse to the heart;
(d) generating at least one further stimulating pulse at the end of a further escape interval measured from the generation of the preceding stimulating pulse;
(e) delivering said stimulating pulses to the patient's heart; and
(f) restarting said first and further escape intervals in response to a sense signal provided during at least a portion of the first or further escape interval or intervals.

14. The method of claim 13 further comprising the steps of:
varying the successive escape intervals between successive stimulating pulses in a predetermined pattern upon the generation of each heart stimulating pulse and upon the restarting of an escape interval in response to a sense signal.

15. The method of claim 14 wherein said step of varying the escape intervals comprises shortening each successive escape interval by a predetermined decrement factor.

16. The method of any of the claims 13-15 wherein the first escape interval is established by:
(a) measuring the tachycardia intervals between successive natural heartbeats;
(b) storing the measured intervals; and
(c) employing the last measured interval as the first escape interval.

17. The method of any of the claims 13-15 wherein the step of confirming a tachycardia further comprises the steps of:
(a) measuring the intervals between successive natural heartbeats against an established threshold beat-to-beat tachycardia value;
(b) counting each measured interval that is shorter than said threshold value; and
(c) confirming the presence of tachycardia when the count of measured intervals shorter than said threshold value exceeds an established count value.

18. The method of any of the claims 1-3 or 13-15 wherein the step of confirming a tachycardia further comprises the steps of:
(a) measuring the rate of change of successive intervals between successive natural heartbeats against an established threshold rate of change value and providing an increment signal each time the measured rate of change exceeds the threshold rate of change value;
(b) counting the increment signals; and
(c) confirming the presence of tachycardia when the count of successive increment signals exceeds an established count value.

19. The method of any of the claims 13-15 wherein the first escape interval is established by:
(a) measuring the tachycardia intervals between successive natural heartbeats;
(b) storing the measured intervals; and
(c) employing the last measured interval as the first escape interval; and wherein the step of confirming a tachycardia further comprises the steps of:
(a) measuring the intervals between successive natural heartbeats against an established threshold beat-to-beat tachycardia value;
(b) counting each measured interval that is shorter than said threshold value; and
(c) confirming the presence of tachycardia when the count of measured intervals shorter than said threshold value exceeds an established count value.

20. A tachycardic control pacer comprising:
(a) sensing means for sensing natural heart depolarizations;
(b) means for confirming a tachycardia condition;
(c) pulse generating means responsive to said confirming means for generating a burst of a plurality of spaced heart stimulating pulses which potentially allows tachycardia to be terminated, said pulse generating means comprising timing means for establishing the escape intervals between the plurality of spaced heart stimulating pulses; and
(d) reset means responsive to said sensing means for resetting said timing means to restart the escape interval in the event that a natural heartbeat is sensed during the provision of said burst of heart stimulating pulses, whereby the provision of a stimulating pulse into a vulnerable phase of the heart is avoided.

21. The apparatus of claim 20 further comprising means for varying the escape intervals between successive stimulating pulses in the burst in a predetermined pattern upon the generation of each heart stimulating pulse in the burst and upon the restarting of an escape interval in response to a sense signal.

22. The apparatus of claim 20 or 21 wherein said means for varying the escape interval comprises means for shortening each successive escape interval by a predetermined decrement factor.

23. Apparatus for detecting and treating a tachycardia condition comprising:
(a) means for sensing natural heart depolarizations and providing sense signals in response thereto;
(b) means for measuring the intervals between successive sense signals and confirming tachycardia as a function of the measured intervals;
(c) means responsive to a confirmed tachycardia for generating a stimulating pulse at the end of a first escape interval measured from a preceding sense signal and applying the pulse to the heart;

(d) means for generating at least one further stimulating pulse at the end of a further escape interval measured from the generation of the preceding stimulating pulse;

(e) means for delivering said stimulating pulses to the patient's heart; and (f) means for restarting said first and further escape intervals in response to a sense signal provided during at least a portion of the first or further escape interval or intervals.

24. The apparatus of claim 23 further comprising means for varying the successive escape intervals between successive stimulating pulses in a predetermined pattern upon the generation of each heart stimulating pulse and upon the restarting of an escape interval in response to a sense signal.

25. The apparatus of claim 24 wherein said means for varying the escape intervals comprises means for shortening each successive escape interval by a predetermined decrement factor.

26. The apparatus of any of the claims 23–25 wherein the first escape interval is established by:

(a) means for measuring the tachycardia intervals between successive natural heartbeats;

(b) means for storing the measured intervals; and (c) means for employing the last measured interval as the first escape interval.

27. The apparatus of any of the claims 23–25 wherein the means for confirming a tachycardia further comprises:

(a) means for measuring the intervals between successive natural heartbeats against an established threshold beat-to-beat tachycardia value;

(b) means for counting each measured interval that is shorter than said threshold value; and (c) means for confirming the presence of tachycardia when the count of measured intervals shorter than said threshold value exceeds an established count value.

28. The apparatus of any of the claims 7–9 or 23–25 wherein the means for confirming a tachycardia further comprises:

(a) means for measuring the rate of change of successive intervals between successive natural heartbeats against an established threshold rate of change value and providing an increment signal each time the measured rate of change exceeds the threshold rate of change value;

(b) means for counting the increment signals; and (c) means for confirming the presence of tachycardia when the count of successive increment signals exceeds an established count value.

29. The apparatus of any of the claims 23–25 wherein the first escape interval is established by:

(a) means for measuring the tachycardia intervals between successive natural heartbeats;

(b) means for storing the measured intervals; and (c) means for employing the last measured interval as the first escape interval; and wherein the means for confirming a tachycardia further comprises:

(a) means for measuring the intervals between successive natural heartbeats against an established threshold beat-to-beat tachycardia value;

(b) means for counting each measured interval that is shorter than said threshold value; and (c) means for confirming the presence of tachycardia when the count of measured intervals shorter than said threshold value exceeds an established count value.

* * * * *